United States Patent
Weiss et al.

(10) Patent No.: US 10,934,324 B2
(45) Date of Patent: Mar. 2, 2021

(54) METHOD FOR IMPROVING PROTEIN FUNCTIONALITY USING VORTEXING FLUID SHEAR FORCES

(71) Applicants: THE REGENTS OF THE UNIVERSITY OF CALIFORNIA, Oakland, CA (US); FLINDERS UNIVERSITY, Bedford Park (AU)

(72) Inventors: Gregory A. Weiss, Irvine, CA (US); Colin L. Raston, Blackwood (AU); Tom Z. Yuan, Los Angeles, CA (US); Callum Ormonde, Nedlands, WA (US); Stephan Timothy Kudlacek, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 656 days.

(21) Appl. No.: 14/913,951

(22) PCT Filed: Sep. 3, 2014

(86) PCT No.: PCT/US2014/053888
§ 371 (c)(1),
(2) Date: Feb. 23, 2016

(87) PCT Pub. No.: WO2015/034915
PCT Pub. Date: Mar. 12, 2015

(65) Prior Publication Data
US 2016/0355545 A1    Dec. 8, 2016

Related U.S. Application Data

(60) Provisional application No. 61/873,718, filed on Sep. 4, 2013.

(51) Int. Cl.
*C07K 1/113* (2006.01)
*C12N 9/36* (2006.01)
(Continued)

(52) U.S. Cl.
CPC ............ *C07K 1/113* (2013.01); *C07K 1/14* (2013.01); *C07K 14/005* (2013.01); *C07K 14/47* (2013.01);
(Continued)

(58) Field of Classification Search
CPC ........ C07K 1/113; C07K 1/14; C07K 14/005; C07K 14/47; C12N 9/2462; C12N 2740/16111; C12Y 302/01017
(Continued)

(56) References Cited

U.S. PATENT DOCUMENTS 3,329,410 A   7/1967   Rothert
4,479,720 A   10/1984  Mochida et al.
(Continued)

FOREIGN PATENT DOCUMENTS

EP    0003907       9/1979
WO    00/48732      8/2000
WO    2012/034164   3/2012

OTHER PUBLICATIONS

SS-34 Rotor Information, Retrieved on Jan. 17, 2018 from < https://www.cif.iastate.edu/sites/default/files/uploads/Other_Inst/Centrifuge/SS-34.pdf >.*
(Continued)

*Primary Examiner* — Benjamin R Whatley
*Assistant Examiner* — Jacqueline Brazin
(74) *Attorney, Agent, or Firm* — Vista IP Law Group LLP

(57) ABSTRACT

A method of improving protein functionality includes obtaining a protein such as protein contained within exclusion bodies contained within bacteria or yeast used for the
(Continued)

recombinant expression of the protein. The exclusion bodies are solubilized using a chaotropic agent such as guanidine or urea. The protein is then subject to denaturation conditions and optionally purified. A liquid containing the denatured protein is loaded into a vessel that is angled relative to horizontal. The vessel is then rotated in the angled configuration at a rate within that is less than 10,000 RPM for period of time. Refolded protein is formed by the high shear conditions formed in the thin film of fluid formed in the inner surface of the rotating vessel. Refolding can be performed in a batch mode or a continuous mode. The process may be scaled up for industrial applications by using multiple vessels.

11 Claims, 11 Drawing Sheets

(51) Int. Cl.
  *C07K 1/14* (2006.01)
  *C07K 14/47* (2006.01)
  *C07K 14/005* (2006.01)
(52) U.S. Cl.
  CPC .... *C12N 9/2462* (2013.01); *C12Y 302/01017* (2013.01); *C12N 2740/16111* (2013.01)
(58) Field of Classification Search
  USPC ........................................................ 422/527
  See application file for complete search history.

(56) References Cited

U.S. PATENT DOCUMENTS

| | | | |
|---|---|---|---|
| 4,831,108 A | 5/1989 | Richardson et al. | |
| 6,756,023 B1 | 6/2004 | Corr et al. | |
| 2002/0061568 A1* | 5/2002 | Machida | C07K 1/1136 435/183 |
| 2004/0038333 A1* | 2/2004 | Randolph | C07K 14/52 435/68.1 |
| 2005/0053532 A1 | 3/2005 | Holl | |
| 2006/0068492 A1* | 3/2006 | Choi | C12M 23/08 435/293.2 |
| 2006/0147357 A1 | 7/2006 | Leveson | |
| 2006/0240061 A1* | 10/2006 | Atala | A61F 2/06 424/422 |
| 2007/0238860 A1* | 10/2007 | Schlegl | C07K 1/1133 530/350 |
| 2010/0185022 A1 | 7/2010 | Raston et al. | |
| 2013/0289282 A1* | 10/2013 | Raston | B01J 19/0093 546/350 |
| 2015/0376229 A1* | 12/2015 | Blum | C07K 1/1136 530/387.3 |
| 2018/0252713 A1 | 9/2018 | Weiss et al. | |

OTHER PUBLICATIONS

Hettich RCF to RPM Calculator—Retrieved from < https://www.hettweb.com/mobile-app > on Jan. 17, 2018.*
Schmid et al., "Expression of porin from Rhodopseudomonas blastica in *Escherichia coli* inclusion bodies and folding into exact native structur", FEBS Letts., 1996, vol. 381, pp. 111-114.*
Jaspe, J. (2006). "Do Protein Molecules Unfold in a Simple Shear FLow?" Biophys. J. 91(9). 3415-3424. (Year: 2006).*
Vallejo, Luis Felipe et al., Strategies for the recovery of active proteins through refolding of bacterial inclusion body proteins, Microbial Cell Factories 2004, 3:11, http://www.microbialcellsfactories.com/content/3/1/11 (12 pages).
PCT International Preliminary Report on Patentability (Chapter I of the Patent Cooperation Treaty) for PCT/US2014/053888, Applicant: The Regents of the University of California, Form PCT/IB/326 and 373, dated Mar. 17, 2016 (7pages).
Jaspe et al., Do protein molecules unfold in a simple shear flow? Biophys J, Nov. 1, 2006, vol. 91, No. 9, pp. 3415-3424.
PCT International Search Report for PCT/US2014/053888, Applicant: The Regents of the University of California et al., Form PCT/ISA/210 and 220, dated Dec. 4, 2014 (4 pages).
PCT Written Opinion of the International Search Authority for PCT/US2014/053888, Applicant: The Regents of the University of California, Form PCT/ISA/237, dated Dec. 4, 2014 (5 pages).
Chen, Xianjue et al., Vortex fluidic exfoliation of graphite and boron nitride, Chem. Commun., 2012, 48, 3703-3705.
Eroglu, Ela et al., Vortex fluidic entrapment of functional microalgal cells in a magnetic polymer matrix, Nanoscale, 2013, 5, 2627-2631.
Hartl, Ulrich et al., Molecular chaperones in protein folding and proteostasis, Nature 475, 324-332 (2011).
Wahid, M. Haniff et al., Functional multi-layer graphene-algae hybrid material formed using vortex fluidics, Green Chem., 2013, 15, 650-655.

* cited by examiner

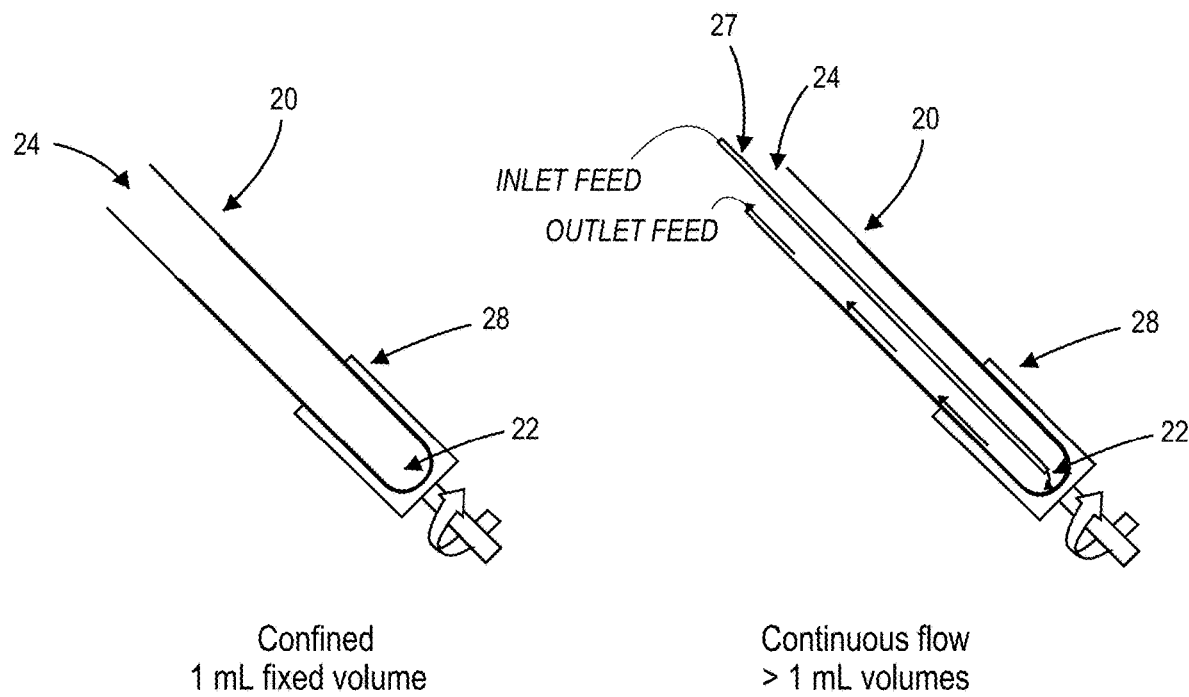

METHOD FOR IMPROVING PROTEIN FUNCTIONALITY USING VORTEXING FLUID SHEAR FORCES

RELATED APPLICATIONS

This Application is a U.S. National Stage filing under 35 U.S.C. § 371 of PCT Patent Application No. PCT/US2014/053888, filed Sep. 3, 2014, which claims priority to U.S. Provisional Patent Application No. 61/873,718 filed on Sep. 4, 2013. The contents of the aforementioned applications are incorporated by reference herein. Priority is expressly claimed in accordance with 35 U.S.C. §§ 119, 120, 365 and 371 and any other applicable statutes.

STATEMENT REGARDING FEDERALLY SPONSORED RESEARCH AND DEVELOPMENT

This invention was made with Government support under Grant Nos. AG023583 and R01 GM100700-01, awarded by the National Institutes of Health. The Government has certain rights in the invention.

FIELD OF THE INVENTION

The field of the invention generally relates methods for improving protein functionality. More particularly, the field of the invention relates to the refolding of proteins such as overexpressed, recombinant proteins from misfolded aggregates.

BACKGROUND

Overexpressed, recombinant proteins for industrial, pharmaceutical, environmental and agricultural applications annually represent a >$160 billion world market. Protein expression in yeast or Escherichia coli (E. coli) is highly preferred due to the organisms' rapid growth, low consumable costs, and high yields. However, large proteins overexpressed in bacteria typically misfold into aggregates, and form insoluble pellets termed inclusion bodies. The inclusion bodies are located in the periplasmic space and can make up a majority of the bacterial cell's total population.

Typically, after isolating a protein from inclusion bodies, a first step in purifying the protein is to solubilize the protein in strong salt concentration using a chaotropic reagent that dissolve and unfold the protein by breaking hydrogen bonding and hydrophobic interactions holding the inclusion body together. The now unfolded protein solution is then later diluted or dialyzed with a refolding buffer to reduce the denaturant concentration allowing the protein to refold. However, a significant pathway to product loss during this refolding step is aggregation. Aggregation occurs when attractive forces between different proteins are more favorable than the attractive forces between protein and solute. The residue-to-residue attractive forces which help refold proteins to their native state unfortunately compete with the unfavorable intermolecular attractive forces resulting in soluble aggregates. The aggregates may then precipitate out. While aggregation of proteins is sometimes reversible such processes require additional costs and take time.

The recovery of the correctly folded protein requires laborious and expensive processing of inclusion bodies by conventional methods. The most common method for refolding such proteins, for example, involves multi-day dialysis with large volumes of media (typically 1 to 10 liters for mg quantities of protein). For example, conventional refolding processes may require repetitive dialysis procedures that can require four (4) days to accomplish. FIG. 1 illustrates a prior art process for protein refolding.

Alternatively, high value proteins, such as therapeutic antibodies or G protein-coupled receptors (GPCRs) for structural biology, apply extensively optimized mammalian or insect cell lines, media and bioreactor conditions. Recovery of correctly folded proteins from aggregates of misfolded proteins derived from such cell lines, and also from bacteria expression, is inefficient and challenging for large-scale industrial processes. While the latter typically offer the highest yields and much lower material, labor and equipment costs, new methods capable of broadening the utility of bacterial over-expression could transform industrial and research production of proteins.

Not having the luxury of switching cell lines to solve this problem; Nature has evolved molecular machines, termed chaperones, to assist with protein folding. One class of these machines, called chaperonins (e.g., GroEL-GroES in E. coli), can reverse protein aggregation and refold proteins through minimization of the thermodynamic energy of unfolding. This assistance is required by essentially all proteins >100 residues in length produced in cells. After binding to the substrate protein, ATP hydrolysis by GroEL triggers unfolding of the misfolded protein. During this step, the chaperonin undergoes a conformational rearrangement to unfold the protein. Then, ATP-dependent binding of the GroES complex allows the targeted protein to refold in ≈10 s while enclosed in a cage-like interior of the chaperonin. Thus, the GroEL-GroES chaperonin system embodies two important concepts—mechanical unfolding and shielding of partially folded intermediates.

U.S. Patent Application Publication No. 2013-0289282 discloses a method and system for in vitro protein folding for larger, commercial production schemes for recovering a refolded protein. The system and method involves the static mixing of a concentrated solution of a denatured protein with a refolding diluent to obtain the refolded protein. The static mixer includes a series of mixing elements in a conduit. The mixing elements are un-powered (i.e., static) and provide mixing action only by the movement of the liquid flow over them. There is a need for alternative methods to improve the functionality of proteins.

SUMMARY

In one embodiment, a method of improving protein functionality includes loading a liquid containing a denatured protein into a vessel that is angled relative to horizontal. The vessel is rotated in the angled configuration at a rate within the range of about 3000 RPM to about 9000 RPM for period of time.

In another embodiment, a method of improving protein functionality includes continuously loading a fluid containing a denatured protein into a vessel that is angled relative to horizontal and rotating the vessel in the angled configuration at a rate within the range of about 3000 RPM to about 9000 RPM for a period of time. A portion of the fluid from the vessel is continuously removed during rotation of the vessel.

BRIEF DESCRIPTION OF THE DRAWINGS

FIG. 5 illustrates one embodiment of a batch mode of operation of the vortex fluid device.

FIG. 6 illustrates another embodiment of a continuous mode of operation of the vortex fluid device.

using Prism 6 software (GraphPad). All assays were conducted in 96-well black well microtiter plates, 100 μL reaction volumes, with 10 min incubation at 37° C.

Figure 9:
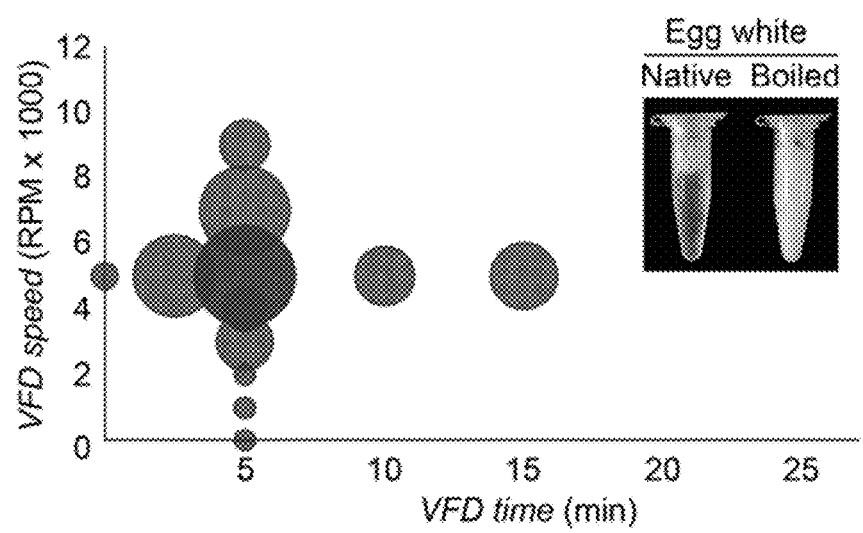

FIG. 9 illustrates a graph illustrating the recovery of activity of boiled egg white and unaltered egg white after treatment with the vortex fluid chaperone (VFD) device with fixed rotational speeds (5,000 rpm) and fixed refolding times (5 min).

Figure 10:
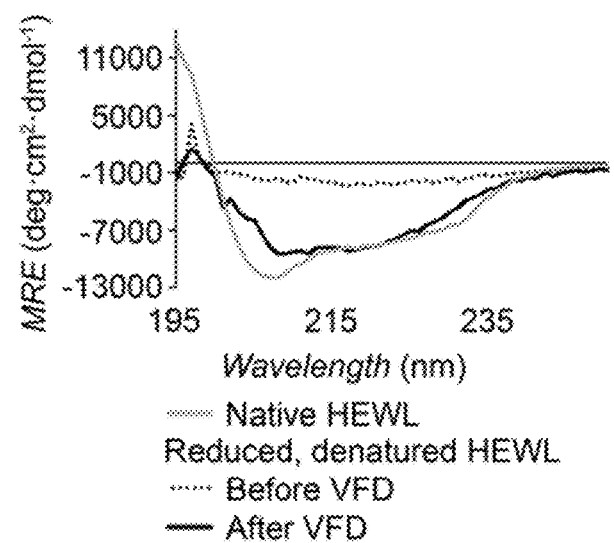

FIG. 10 illustrates Circular dichroism (CD) spectra of recombinantly expressed hen egg white lysozyme (HEWL) with and without VFD-induced refolding (5000 rpm, 5 min, 22° C.).

Figure 11:
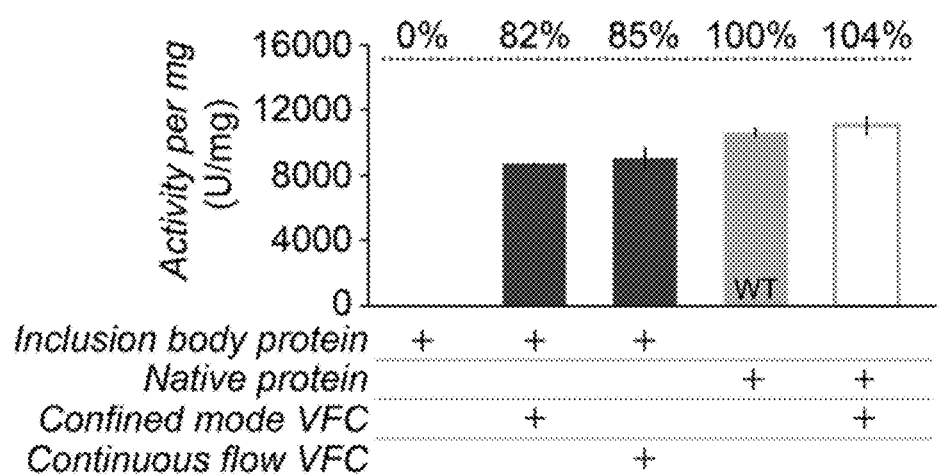

FIG. 11 illustrates lysozyme activity per mg protein following VFD-induced refolding of recombinantly expressed HEWL for both the batch and continuous (5000 rpm, 22° C., 1 mL batch mode, 50 mL continuous mode with flow at 0.1 mg/mL). Compared to native lysozyme, HEWL refolded from the inclusion body recovered over 82% of activity, as measured by activity per mg of protein from both the confined and continuous flow modes of VFD-induced refolding (5000 rpm, 1 mL for 5 min confined mode, 50 mL at 0.1 mg/mL for continuous flow, 22° C.). Error bars indicate standard deviation (n=3).

Figure 12:
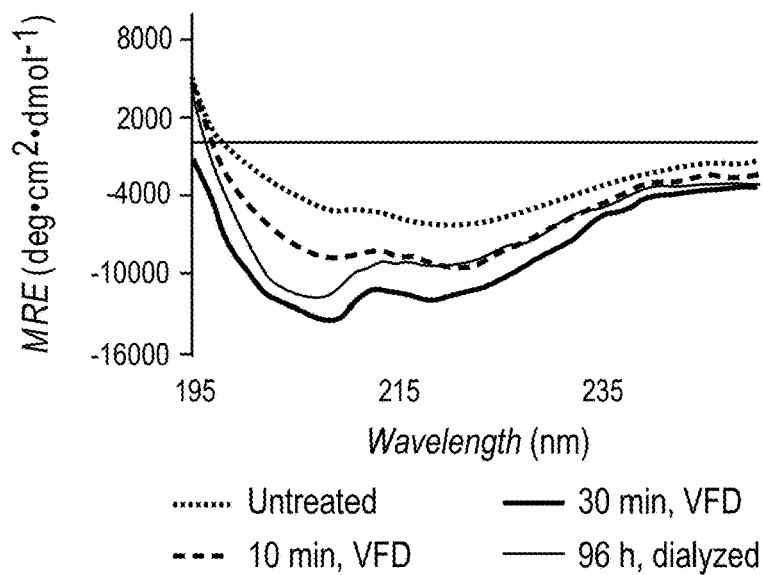

FIG. 12 illustrates CD spectra of caveolin-ΔTM measured without VFD-induced refolding and with VFD-induced refolding (5000 rpm, 10 min or 30 min, 22° C.).

Figure 13:
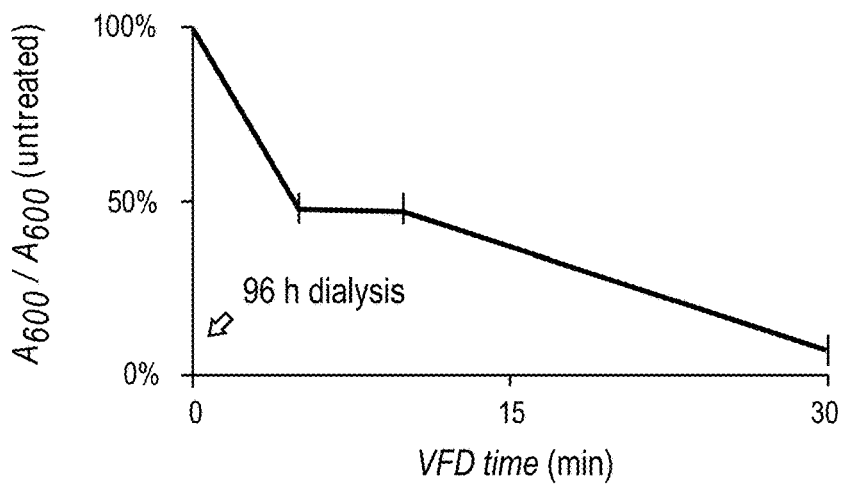

FIG. 13 illustrates absorbance at 600 nm of protein samples (as a percentage of absorbance of untreated caveolin-ΔTM) at 0, 5, 10, or 30 min VFD refolding times under the same conditions. The experiment demonstrates decreased levels of turbidity, resulting from increased protein solubility through VFD treatment.

Figure 14:
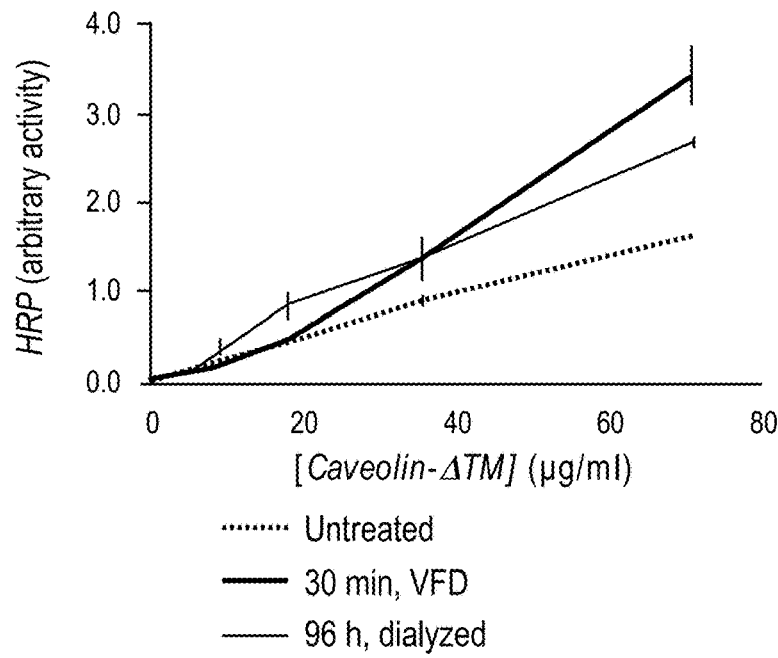

FIG. 14 illustrates a graph of the dependent binding of unprocessed, processed, and conventionally refolded caveolin-ΔTM to HIV gp41 determined by ELISA. Although some binding occurs without any VFD processing, caveolin-ΔTM binds with greater affinity after VFD refolding (5000 rpm, 30 min, 22° C.).

Figure 15:
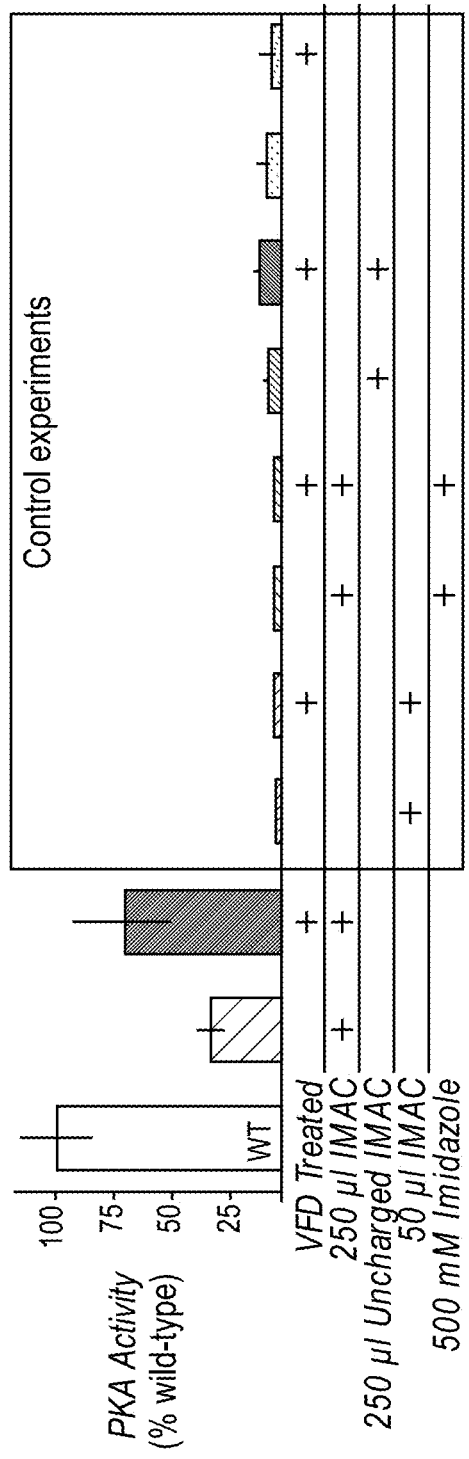

FIG. 15 illustrates a bar graph illustrating VFD facilitating the refolding of PKA by pre-binding to IMAC resin. 1.7 mg PKA was pre-incubated with 250 or 50 μl IMAC resin in 6 M guanidine-HCl prior to dilution to 1 M guanidine-HCl and VFD treatment. Excess PKA is removed by a low imidazole (1 mM) wash buffer. PKA activity per μg of protein measured by nicotinamide adenine dinucleotide (NADH) enzyme-linked assay and shown as percentage of wild-type PKA. Consumption of ATP by active PKA results in consumption of NADH by lactate dehydrogenase. The NADH levels are monitored in this assay by absorbance at 340 nm. Negative control experiments were performed with low quantities of resin, 500 mM imidazole, or resin lacking $Ni^{2+}$ (uncharged) during IMAC incubation.

Figure 16:
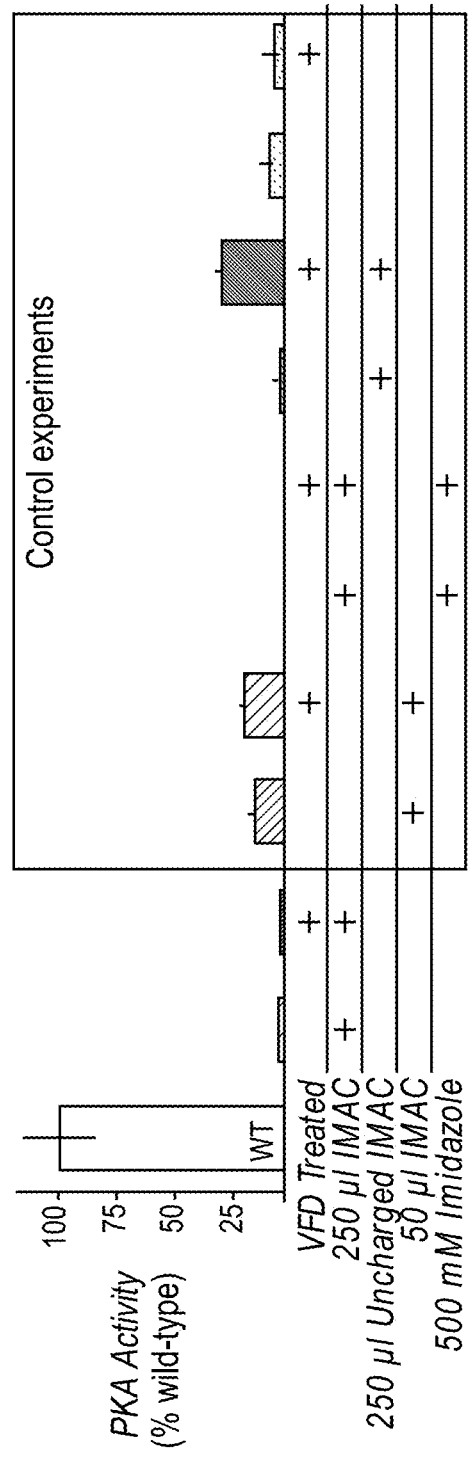

FIG. 16 illustrates kinase activity per μg of PKA, measured by consumption of NADH, of elution fractions following VFD treatment. 1.7 mg PKA was pre-incubated with 250 or 50 μl IMAC resin in 6 M guanidine-HCl prior to dilution to 1 M guanidine-HCl and VFD treatment. Excess PKA is removed by a low imidazole (1 mM) buffer, and remaining PKA eluted by high imidazole (500 mM) buffer. Control experiments were performed with low resin, 500 mM imidazole, or uncharged IMAC resin during IMAC incubation.

DETAILED DESCRIPTION OF THE ILLUSTRATED EMBODIMENTS

Figure 1:
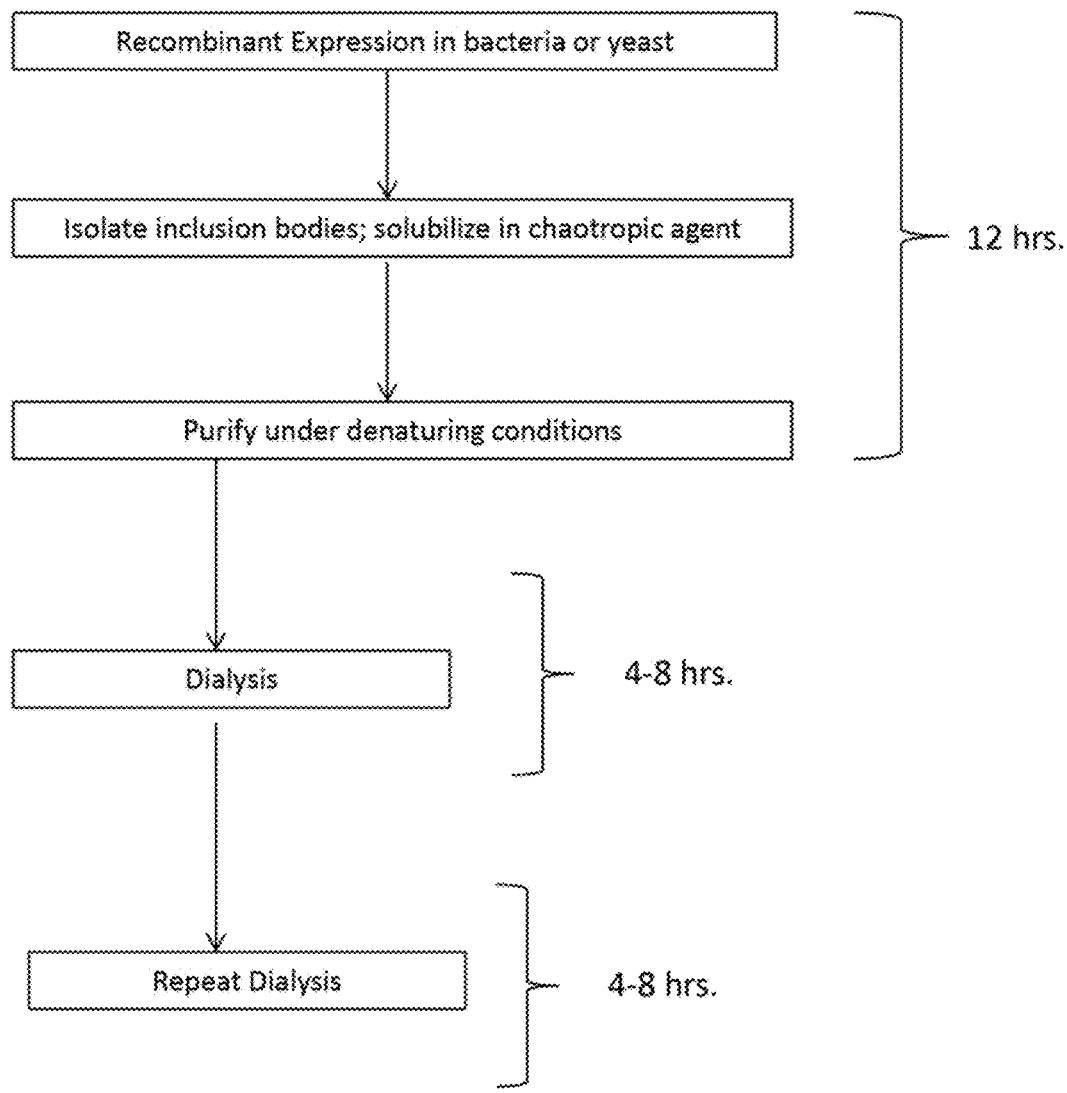
FIG. 1 illustrates a prior art process for protein refolding.
Figure 2:
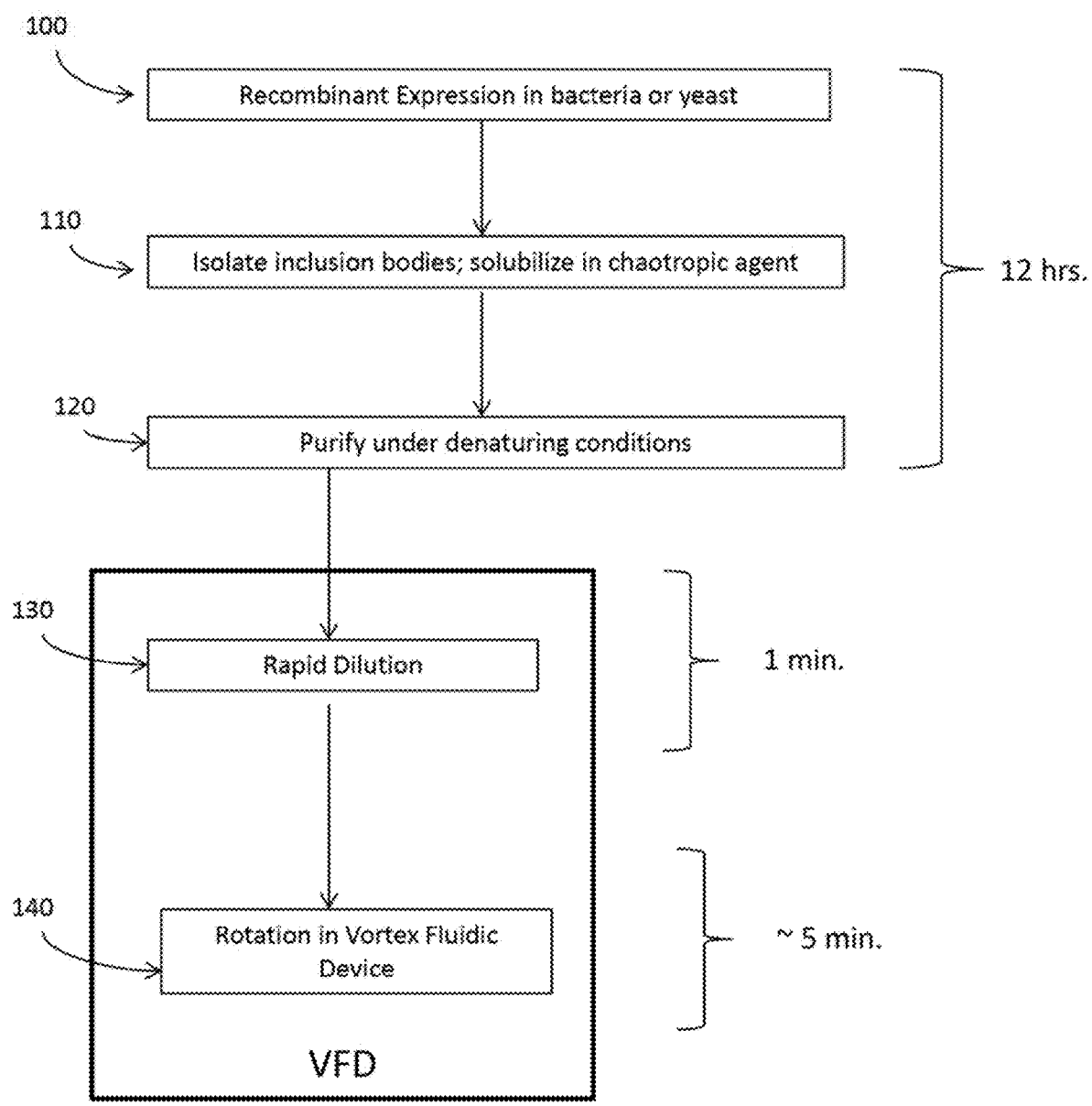
FIG. 2 illustrates a process for improving protein functionality according to one embodiment of the invention.

FIG. 2 illustrates a process for improving protein functionality according to one embodiment. Improving protein functionality encompasses refolding of misfolded proteins. Improving protein functionality also encompasses improving protein activity of native or even purified proteins. Improved protein functionality extends to improved catalytic or enzymatic activity. Even in commercially available proteins, activity of proteins may be improved by the methods described herein. In this embodiment protein refers to recombinantly expressed protein from a host cell such as *E. coli* or yeast although the protein does not have to be recombinantly generated. As explained herein, protein that is recombinantly expressed within such hosts often aggregates within inclusion bodies. The proteins within the inclusion bodies are often misfolded. In order for the proteins to regain native functionality, the misfolded proteins need to be refolded and this method accomplishes that goal. As seen in FIG. 2, in operation 100 protein is recombinantly expressed in *E. coli*. Next, as seen in operation 110, inclusion bodies contained within the *E. coli* are isolated using centrifugation or any other process typically used to collect inclusion bodies. The inclusion body is solubilized using a chaotropic agent. Examples of chaotropic agents include guanidine and urea, although the invention is not limited to the type of chaotropic agent. In operation 120, the solubilized protein is optionally purified under denaturing conditions. As noted, this operation is optional and in some instances purification is not needed. When purification is used, typically, the solubilized protein can be purified using an exchange resin process wherein the protein can then be washed and eluted. The purified, denatured protein is then optionally diluted in operation 130. Typically a buffer solution such as phosphate buffered saline (PBS) is used. In some instances, dilution is not necessarily required. Next, as seen in operation 140, the protein is loaded into a device called a vortex fluid device (VFD), which is described in more detail below, which operates to apply mechanical energy through the high-speed rotation of fluid in a vessel to create intense shear forces to unfold inactive protein and allow recovery of natively folded protein.

Figure 3:
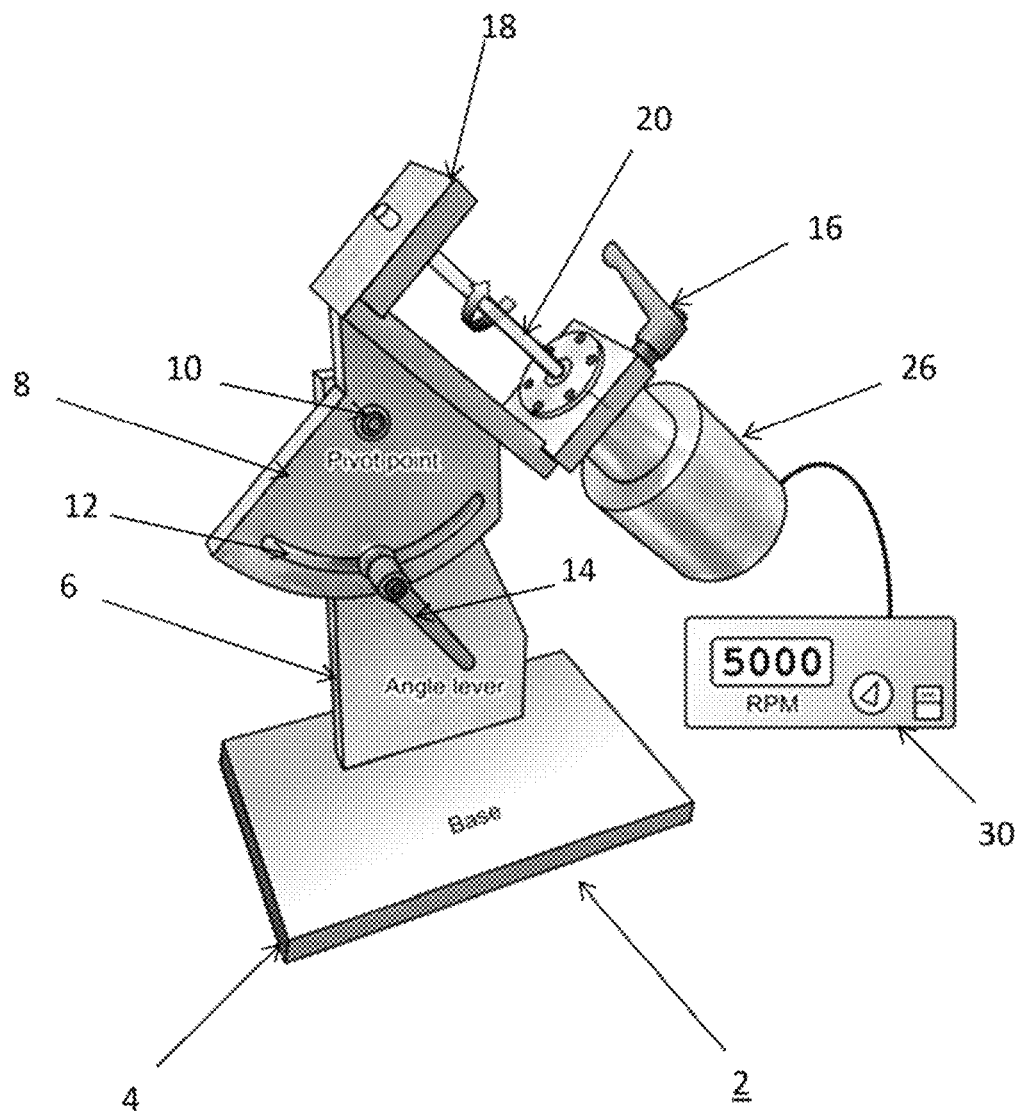
FIG. 3 illustrates one embodiment of a vortex fluid device that applies mechanical energy to generate intense microfluidic shear forces to unfold inactive protein and allowing recovery of natively folded protein from inclusion bodies in less than 5 minutes.

FIG. 3 illustrates a VFD 2 according to one embodiment. The VFD 2 includes a base 4 along with a vertical support 6. A pivot plate 8 is mounted to the vertical support 6 via a pivot 10. The pivot plate 8 includes an arcuate-shaped slot 12 that contains a fastener 14 that can be selectively tightened (or loosened) to adjust the angle of the pivot plate 8 relative to the vertical support 6. When the desired angle is reached, the fastener 14 such as the illustrated lever can be tightened to lock the pivot plate 8 relative to the vertical support 6. A clamp 16 and spinning guide 18 are secured to the pivot plate 8 and are configured to hold a vessel 20 in an angled orientation as illustrated in FIG. 3 by adjustment of the pivot plate 8 as described herein. The spinning guide 18 assists in maintaining the angle of incline θ relative to horizontal (seen in FIGS. 4A and 4B) and a substantially constant rotation around the longitudinal axis of the vessel 20. The angle of incline θ may vary but is typically between about 20° and 70° with optimum results typically being generated at about 45° (all with respect to horizontal).

Figure 4A:
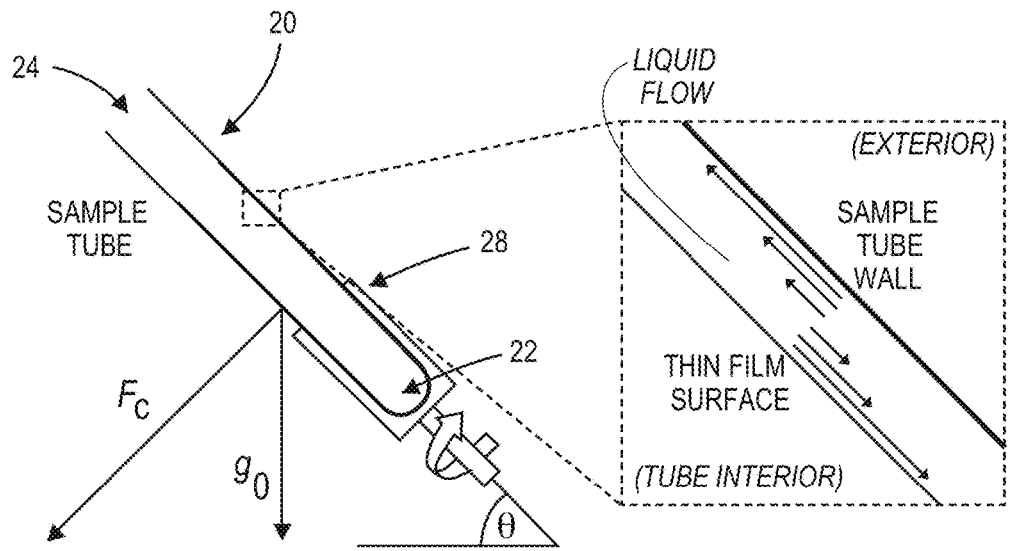
FIG. 4A illustrates a schematic representation of a vessel being rotated about a long axis to generate a thin film of fluid on an inner surface of the vessel wall along with a magnified view of thin film conditions along the interior surface of the vessel.
Figure 4B:
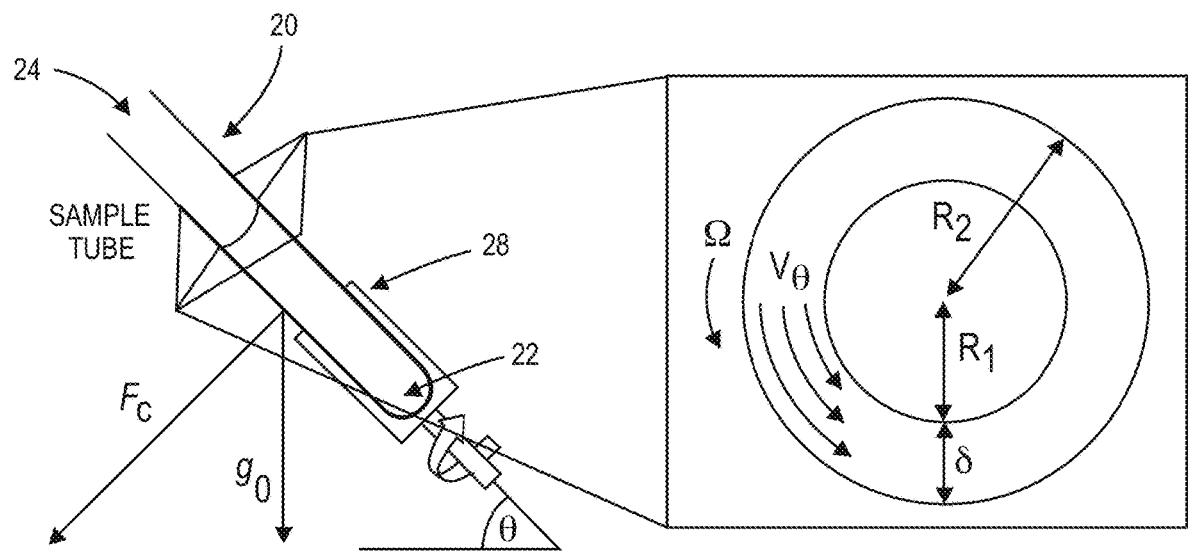
FIG. 4B illustrates a schematic representation of a vessel being rotated about a long axis to generate a thin film of fluid on an inner surface of the vessel wall along with a magnified view of a two-dimensional cross-section of the vessel.

As best seen in FIGS. 4A and 4B, the vessel 20 is configured to hold a fluid therein and includes a closed end 22 and an open end 24. The vessel 20 includes an internal wall where a thin film of fluid is formed when the vessel 20 is rotated. The vessel 20 has a circular-shaped cross section and may take the form of a tube. For example, the vessel 20 may be formed from a glass tube. The vessel 20 may have a diameter (internal diameter) of around 10 mm although other sizes are contemplated. For example, for larger scale operations, a larger vessel 20 with a diameter of 20 mm or more may be used. The length of the vessel 20 may vary as well. For example, the vessel 20 may have a length of around 20 cm (e.g., 16 cm) although the length may vary depending on the particular application. In one alternative embodiment, the inner surface of the vessel 20 may be textured or have a modified surface with protuberances creating high contact angles that can enhance turbulent flow and/or alter the applied shear stress.

Referring back to FIG. 3, the closed end 22 of the vessel 20 is coupled to a motor 26 via a chuck 28 (seen in FIGS. 4A and 4B). Rotation of the motor 26 causes rotation of the chuck 28 and thus the vessel 20. The motor 26 may be operably coupled to a controller 30 that can be used to turn the motor 26 on/off and adjust the rotational speed of the motor 26 and vessel 20. The motor 26 preferably can be adjusted to spin the vessel 20 between 0 and 10,000 rpm although higher speeds are also contemplated to fall within the scope of the invention. In the experimental results described herein, optimal results were achieved at around 5,000 rpm although this number may change depending on the dimensions of the vessel 20 that is used as well as the protein that is processed. Rotation may occur in either the clockwise or counter-clockwise direction. The controller 30 may be programmed to ramp up to a set-point rotational speed and stay there for a predetermined amount of time and then ramped down to stop rotation. Additional programs may be loaded or otherwise stored within the controller 30.

The VFD 2 refolds proteins or enhances protein folding through applying high shear forces to allow equilibration of protein folding and to isolate folding intermediates. To generate the high mechanical shear forces in liquid media, the vessel 20 is spun rapidly (e.g., at around 5,000 rpm) at an angle θ relative to horizontal. At high rotational speeds, the liquid within the sample tube forms micrometer-thick, thin fluid films as seen in FIG. 4A (inset of FIG. 4A). Inside the microfluidic films, the interaction between centrifugal and gravitational forces generates a strong shearing effect. As determined by fluid dynamics, liquid flow is driven up the side of the rotating tube and gravity forces the liquid back, forming Stewartson/Ekman layers. Unlike high energy indiscriminate cavitation using sonication or other pressure-based disaggregation, the VFD 2 provides a constant 'soft' mechanical energy which pushes the layers apart into solution.

Modeling the fluid behavior in the VFD 2 allows estimation of the shear forces experienced by proteins folding at various rotational speeds. Using the solution for cylindrical Couette flow, the velocity of the solution, $v_\theta$, is a function of the radius, r and the boundary conditions for the liquid film interfaces are defined as follows. The inner air-liquid interface at $r=R_1$ slips due to discontinuity in viscosity, and results in vanishingly low shear stress $$\left(\frac{dv_\theta}{dr} = 0\right).$$

At the outer liquid-glass interface, the no-slip boundary dictates that the velocity of the liquid at $r=R_2$ matches that of the inner wall of the vessel ($v_\theta=R_2\cdot\Omega$) where $\Omega$ is the angular velocity of the tube. The resulting velocity profile is a nonlinear function of the form $$v_\theta = Ar + \frac{B}{r}$$

Where $$A = \frac{\Omega}{\frac{R_1^2}{R_2^2}+1} \text{ and } B = \frac{\Omega R_1^2}{\frac{R_1^2}{R_2^2}+1}$$

From this velocity profile, shear stress can be calculated as:

$$\tau_{r\theta} = \mu r \frac{\partial}{\partial r}\left(\frac{v_\theta}{r}\right)$$

Where μ is the viscosity of water at 20° C. FIG. 4B illustrates a schematic representation of the vessel 20 in the VFD 2 and parameters used for modeling (δ is the thickness of the fluid film and not drawn to scale). At a speed of 5,000 rpm, the calculated shear stress ranges from 0.5246 to 0.5574 Pa. These values of shear stress are similar to the requirements previously reported for protein unfolding.

Figure 7:
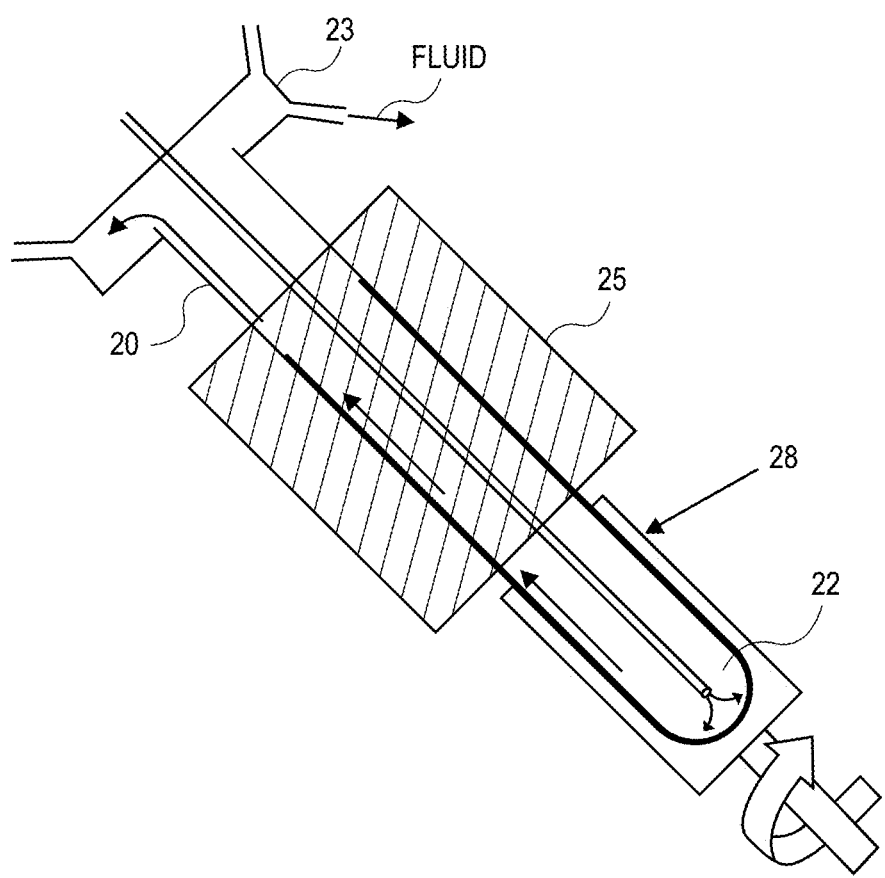
FIG. 7 illustrates another embodiment of a vortex fluid device that uses a thermal jacket.

FIGS. 5 and 6 illustrate two different modes in which the VFD 2 may be run. FIG. 5 illustrates the VFD 2 being used in a batch mode. In the batch mode a fixed volume of fluid containing protein is loaded into the vessel 20 and then run on the VFD 2. During rotation of the vessel 20, the fluid remains inside and does not escape. After rotating for the requisite amount of time, rotation of the vessel 20 is stopped and the fluid can then be emptied or extracted. FIGS. 6 and 7 illustrate an alternative embodiment that is a continuous mode. In the continuous mode embodiment, fluid containing protein is continuously introduced into the vessel 20 using a thin, hollow metal tube (inlet tube 27) that extends inside the vessel 20 and terminates near the closed end 22. During rotation of the vessel 20 fluid travels up the side of the internal wall of the vessel 20 and exits the open end 22 of the vessel 20. As seen in FIG. 7, a collector 23 that is placed substantially adjacent to the open end 22 of the vessel 20 can be used to collect fluid which can then exit via one or more ports as shown. Additional details regarding the collector that may be used with the VFD 2 may be found in U.S. Patent Application Publication No. 2013-0289282, which is incorporated by reference herein.

The continuous mode operation described above is more applicable to large scale operations. The continuous flow mode can introduce additional shear forces from the viscous drag as the injected liquid whirls along the vessel 20, and also allows processing of large volumes of solution, with the device 2 having a small foot print and low capital outlay. In addition, while FIGS. 5 and 6 illustrate a single VFD 2 device with a single vessel 20, it should be understood that the process can be scaled-up with additional VFD 2 devices. For example, large processing may require a plurality of vessels 20. Each vessel 20 may be driven by its own dedicated motor 26 or, alternatively, vessels 20 may be coupled through appropriate gearing, belts, or the like to be driven by a common or shared motor 26 or multiple shared motors 26. The vessels 20 may be arrayed together or otherwise arranged to form a unitary system in which each vessel 20 of the array can be operated at the same operating conditions.

In some embodiments, as illustrated in FIG. 7, the temperature of the vessel 20 may be controlled through the use of a jacket 25 that partially or wholly surrounds the circumference of the vessel 20 for heating and/or cooling of the vessel 20. The jacket 25 may also be used to insulate the vessel 20 from the external environment. Details regarding a suitable jacket 25 may be found in U.S. Patent Application Publication No. 2013-0289282 which is incorporated by reference herein. Heat may also be applied without the jacket 25. For example, an external energy source such as the application of vibrational energy or electromagnetic energy may be used to adjust the temperature of the vessel 20.

Experimental

Experiments with native hen egg white were conducted to determine if shear forces could refold denatured hen egg white lysozyme (HEWL) in complex environments. The separated whites were diluted in PBS, and heat-treated at 90° C. for 20 min. The resultant hard-boiled egg white was dissolved in 8 M urea, rapidly diluted and then VFD processed at the indicated rotational speeds and times at Table 1 below. Table 1 shows the lysozyme activity per mg of total protein following VFD refolding of boiled egg whites (treated at 90° C. for 20 min) and native egg white. Experiments were conducted with fixed VFD speed at 5 krpm and variable time as well as fixed 5 min refolding time at the variable VFD speeds as indicated (190 µg/ml total protein, PBS, 15 mM, GSH 0.5 mM GSSG, 22° C.).

TABLE 1

| | 90° C. treated egg white | | | | | Native egg white | | | |
|---|---|---|---|---|---|---|---|---|---|
| Time (m) | Speed (rpm × 1000) | Activity (U/mg) | Std. Dev. | % | Time (m) | Speed (rpm × 1000) | Activity (U/mg) | Std. Dev. | % |
| | | | | Fixed speed, variable time | | | | | |
| 0 | 5 | 25.17 | 11.56 | 1.0% | 0 | 5 | 2649.35 | 432.80 | 100.0% |
| 2.5 | 5 | 238.78 | 36.62 | 9.0% | 2.5 | 5 | 2482.34 | 298.14 | 93.7% |
| 5 | 5 | 364.93 | 27.52 | 13.8% | 5 | 5 | 2725.92 | 756.38 | 102.9% |
| 10 | 5 | 125.62 | 15.14 | 4.7% | 10 | 5 | 2064.42 | 168.00 | 77.9% |
| 15 | 5 | 159.23 | 109.97 | 6.0% | 15 | 5 | 2250.25 | 275.44 | 84.9% |
| 30 | 5 | 0.00 | 0.00 | 0.0% | 30 | 5 | 2158.75 | 212.99 | 81.5% |
| | | | | Fixed time, variable speed | | | | | |
| 5 | 0 | 16.11 | 10.34 | 0.6% | 5 | 0 | 2479.12 | 211.10 | 100.0% |
| 5 | 1 | 15.90 | 6.87 | 0.6% | 5 | 1 | 1997.07 | 121.39 | 80.6% |
| 5 | 2 | 15.32 | 6.11 | 0.8% | 5 | 2 | 1680.03 | 82.96 | 67.8% |
| 5 | 3 | 113.93 | 25.07 | 4.6% | 5 | 3 | 1609.84 | 44.08 | 64.9% |
| 5 | 4 | 70.14 | 17.69 | 2.8% | 5 | 4 | 1653.37 | 120.44 | 66.7% |
| 5 | 5 | 353.62 | 118.90 | 14.3% | 5 | 5 | 1561.79 | 83.94 | 63.0% |
| 5 | 7 | 288.21 | 81.54 | 11.6% | 5 | 7 | 1568.70 | 264.62 | 63.3% |
| 5 | 9 | 87.48 | 37.36 | 3.5% | 5 | 9 | 1654.56 | 314.61 | 66.7% |

Figure 8:
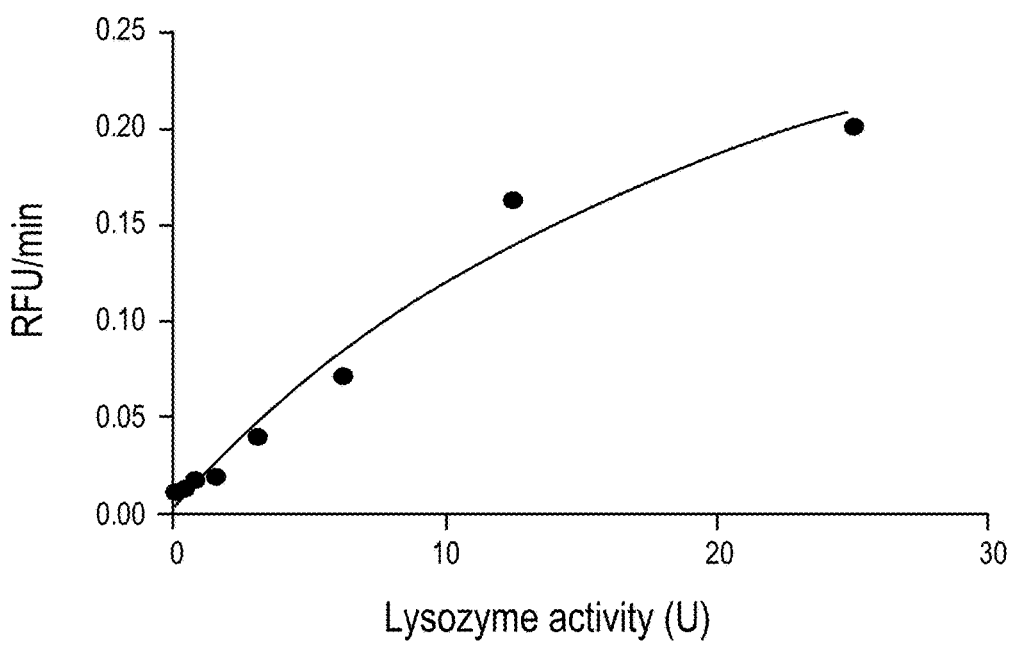
FIG. 8 illustrates lysozyme activity interpolated by least-squares regression fit. The relative fluorescence units per minute was fit to standardized lysozyme activity assayed using the EnzChek Lysozyme Activity kit (Invitrogen) to a Michaelis-Menten curve plus background $$v = \frac{V_{max}[S]}{K_m + [S]}$$

Total protein concentration as determined by bicinchoninic acid assay was 44 µg/ml. FIG. 8 illustrates the recovery of HEWL activity as demonstrated by lysozyme activity assay. Refolding HEWL within the egg white at 5 krpm recovers activity even after a short 2.5 min spin, but continued shear forces unfolds the protein. VFD processing for 5 minutes at 5 krpm results in optimal HEWL refolding as seen in FIG. 9. This experiment establishes parameters for protein refolding by VFD.

To demonstrate refolding of recombinantly expressed, reduced HEWL, the cell pellet was reconstituted in lysis buffer containing 2-mercaptoethanol, purified, urea-denatured and rapidly diluted into PBS (1:100) as seen in Table 2 below.

TABLE 2

| Protein | Expression time (h) | Expression temp. (° C.) | [IPTG] (M) | Lysis buffer |
|---|---|---|---|---|
| Hen egg white lysozyme | 4 | 37 | 1 | 50 mM $NaH_2PO_4$, 500 mM NaCl, 10 mM imidazole, 1 mM HALT protease inhibitor (Pierce), 10 mM 2-mercaptoethanol, pH 8.0 |

TABLE 2-continued

| | | | | |
|---|---|---|---|---|
| Caveolin-ΔTM | 3 | 37 | 0.5 | 50 mM Tris-HCl, 10 mM NaCl, 5 mM EDTA, 100 mM PMSF, pH 8.0 |
| HIV gp41 | 8 | 22 | 0.5 | 50 mM NaH$_2$PO$_4$, 300 mM NaCl, 10 mM 2-mercaptoethanol, 1 mM HALT protease inhibitor, pH 8.0 |
| His-PKA | 5 | 37 | 1 | 50 mM NaH$_2$PO$_4$, 500 mM NaCl, 10 mM imidazole, 1 mM HALT protease inhibitor, 10 mM 2-mercaptoethanol, pH 8.0 |

| Protein | Resin | Denaturing buffer | Binding/wash buffer | Elution buffer |
|---|---|---|---|---|
| Hen egg white lysozyme | UNOsphere S (Bio-Rad) | 20 mM Tris, 10 mM NaCl, 8M urea, pH 7.8 | 20 mM Tris, 10 mM NaCl, 8M urea, pH 7.8 | Wash buffer, 400 mM NaCl |
| Caveolin-ΔTM | Ni-NTA (Bio-Rad) | 50 mM Tris, 50 mM NaCl, 8M urea, pH 8.0 | 50 mM Tris-HCl, 300 mM NaCl, 10 mM imidazole, 0.2% Na azide, 8M urea, pH 8.0 | Wash buffer, pH 4.0 |
| HIV gp41 | Ni-NTA | — | 50 mM NaH$_2$PO$_4$, 300 mM NaCl, 10 mM 2-mercaptoethanol, 20 mM imdazole, pH 8.0 | Wash buffer, 250 mM imidazole |
| His-PKA | Ni-NTA | 20 mM NaH$_2$PO$_4$, 500 mM NaCl, 6M guanidine-HCl, pH 7.0 | 50 mM NaH$_2$PO$_4$, 300 mM NaCl, 1 mM imdazole, pH 7.0 | Wash buffer, 500 mM imidazole |

Second, the diluted protein (1 ml, 44 µg/ml) was immediately transferred to the VFD sample tube and spun at 22° C. and 5 krpm for 5 min. Circular dichroism (CD) spectra of the VFD-refolded, recombinant HEWL demonstrates restoration of secondary structure from proteins isolated from inclusion bodies. After VFD processing, the CD spectra of identical HEWL samples demonstrates partial recovery of secondary structure compared to the native lysozyme as seen in FIG. 10. FIG. 11 illustrates the yields determined by protein activity assay. Note that as seen in FIG. 11, VFD treatment of purified, active lysozyme does not adversely affect its activity. In fact, as seen in FIG. 11, native lysozyme that was subject to VFD treatment actually achieved an activity level of 104% as compared the non-treated control. This demonstrates the ability of VFD to improve protein functionality, even for purified, commercially available native proteins.

HEWL can also be refolded by continuous flow VFD. This approach delivers additional fluid sample through an inlet located at the cylinder base. The sample (50 ml), added at a flow-rate of 0.1 ml/min, demonstrates significant recovery of HEWL activity for scalable, high volume applications. The recombinant HEWL recovers >82% of its activity following VFD treatment. HEWL isolated from inclusion bodies without VFD processing fails to show any lysozyme activity as seen in FIG. 11. As noted herein, the continuous flow approach could be scaled up for industrial applications.

After refolding denatured lysozyme in both complex (egg white) and simple (purified recombinant protein) environments, the next experiments focused on refolding the protein caveolin-1, as an example of a protein requiring an inordinate amount of processing time by conventional approaches (e.g., four days of dialysis using current techniques). A caveolin variant without its transmembrane domain (caveolin-ΔTM) was recombinantly expressed, and the inclusion body was purified under denaturing conditions. Purified caveolin-ΔTM was diluted, and then given a short dialysis for 1 h to lower the urea concentration. The protein was then VFD-treated for 0, 10, or 30 min at 5 krpm at a concentration of 186 µg/ml. The CD spectra of the VFD processed caveolin-ΔTM shows a pronounced minima at 208 nm, which is indicative of α-helical secondary structure as seen in FIG. 12. Solution turbidity also decreases sharply following VFD treatment, which illustrates VFD solubilization and refolding of partially aggregated proteins (FIG. 13). ELISA experiments examined binding by the refolded caveolin-ΔTM to HIV glycoprotein 41 (gp41), a known caveolin binding partner. VFD processing significantly restores protein function, as shown through binding to gp41 as seen in FIG. 14.

Larger-sized proteins initially failed to refold despite VFD treatment. For example, the catalytic domain of PKA (42 kDa) is significantly bulkier than HEWL (14 kDa) and caveolin-ΔTM (17 kDa), and did not refold from inclusion bodies after treatment following similar protocols. To refold full-length PKA in vitro, it was hypothesized that a closer mimic of cellular folding was required. In cells, the nascent polypeptide can fold as the N-terminus extrudes from the ribosome, whereas in vitro refolding must address the entire protein at once. Thus, shear stress was focused on the N-terminus of His-tagged PKA by immobilization on Ni$^{2+}$-charged immobilized metal affinity chromatography (IMAC) beads. The IMAC-His-PKA complex was then subjected to shear stress in the VFD (1 ml, 0.2-1 mg/ml). Following VFD treatment, His-PKA separated from the IMAC resin, and recovered 69% of its kinase activity as seen in FIG. 15. Interestingly, the remaining His-PKA eluted from the IMAC resin by elution with imidazole yielded far less active protein (FIG. 16). Negative control experiments with identical conditions, but with uncharged IMAC resin, lower charged resin volumes, or 500 mM imidazole to block the Ni$^{2+}$-His$_6$ tag interaction, showed only low levels of kinase activity (FIG. 16).

Protein refolding by VFD requires optimization for each protein. Buffers, protein concentration, and processing time were optimized for HEWL, caveolin-ΔTM, and PKA. The refolding of HEWL from the complex mixture of boiled egg whites appears less efficient than recovery of the folded protein from inclusion bodies. This may be explained by the fact that, in egg whites, the mechanical energy of the VFD could be misdirected to the other >96% of proteins present.

Protein processing by VFD offers significant advantages over conventional approaches to protein refolding. First, VFD-mediated refolding requires much smaller solution volumes (approximately 1% of the volumes required for conventional dialysis). Second, this key step in protein production occurs >100-times faster than overnight dialysis with >1000-fold improvements for proteins such as a caveolin. Notably, introducing high shear in thin fluid films is a low energy, inexpensive process.

The advantages of VFD refolding open new possibilities for increasing protein yields in simple cell lines. The VFD can untangle complex mixtures, aggregates and insoluble inclusion bodies. Illustrating this advantage, high concentrations of a chemical inducer like IPTG could drive overexpressed proteins into insoluble inclusion bodies. Most processes would avoid inclusion bodies by optimization of growth conditions and special cell lines at the expense of higher yields and purer protein. Furthermore, the continuous flow mode of the VFD readily allows scale-up to accommodate much larger solution volumes, and the approach could drastically lower the time and financial costs required to refold inactive proteins at an industrial scale. The VFD sample tube or vessel itself can also be modified to amplify or otherwise direct the intensity of shear forces applied; for example, modified surfaces with high contact angle and/or with textured features could enhance the turbulent flow, altering the applied shear stress. Harnessing shear forces to achieve rapid equilibration of protein folding could be expanded to a wide-range of applications for research and manufacturing.

General Materials and Methods

Expression and Purification of Hen Egg White Lysozyme, Caveolin-ΔTM, and HIV gp41

Hen egg white lysozyme (HEWL), caveolin-ΔTM, and HIV gp41 were overexpressed in BL21 E. coli by induction with isopropyl β-D-1-thiogalactopyranoside (IPTG, 1 mM). The 1l culture volume was centrifuged at 6000 rpm to collect the bacterial pellet. The pellet was reconstituted in lysis buffer and sonicated in 30 s continuous bursts with 1 min cooling on ice for eight cycles (20 watts). HEWL and caveolin-ΔTM were purified under denaturing conditions, and HIV gp41 was purified under non-denaturing conditions. For specific expression and purification conditions, see Table 2. The egg whites were obtained from chicken eggs, and diluted 2:3 in PBS, heat-treated at 90° C. for 20 min, and dissolved in 8 M urea overnight at 4° C. The $His_6$ tag was cleaved from HIV gp41 with Tobacco Etch Virus protease, which was then removed by IMAC. All protein concentrations were determined by bicinchoninic acid assay kit (Pierce Chemical Co.).

Protein Refolding and Determination of Native State Confirmation

Commercial, lyophilized HEWL protein (Sigma) was reconstituted in PBS as 'active' HEWL sample. Recombinantly expressed HEWL was pre-treated by 1:100 rapid dilution in PBS, and then refolded by VFD treatment. All samples were treated at 22° C. within a 16 cm long, 10 mm diameter glass test tube. When operated in confined mode, the VFD was set to a 45° tilt angle and 1 ml was spun at 5 krpm, unless otherwise noted. The continuous mode experiment was conducted by flowing the rapidly diluted protein through the inlet port to the base of the sample tube at a flow rate of 0.1 ml/min. Caveolin-ΔTM VFD refolding was performed in confined mode (1 ml, 5 krpm, 22° C.). For comparison, caveolin-ΔTM was also refolded using conventional dialysis over 4 days (1:500, 50 mM Tris-HCl, 1 mM EDTA, 4° C., pH 8.5).

Circular dichroism spectra of HEWL were collected immediately following VFD refolding in PBS (20 nm/min, 4 accumulations), and caveolin-ΔTM were collected in 10 mM sodium phosphate, pH 7.5 (10 nm/min, 8 accumulations). All lysozyme activity assays used the EnzChek kit (Invitrogen) after rapid dilution from denatured protein solution into PBS (1:100) according to manufacture instructions, except for decreasing the 37° C. incubation time from 30 to 10 min. Lysozyme activity was interpolated by least-square regressions fit of lysozyme standards to a Michaelis-Menten curve $$\left( v = \frac{V_{max}[S]}{K_m + [S]} + c \right)$$

with Prism 6 software (GraphPad, FIG. 8). After 1:100 rapid dilution into PBS, protein solution contains 80 mM urea, 0.2 mM Tris and 4 mM NaCl. Lysozyme activity with various levels of urea, Tris, and NaCl was determined to verify that the assay was not affected. Purified caveolin-ΔTM from the inclusion body were diluted 1:5 in 10 mM sodium phosphate, pH 7.5 and then briefly dialyzed prior to VFD treatment (1:100 volume, 1 h, 4° C.) for circular dichroism spectra.

ELISA Binding Assays

The dose-dependent ELISA was conducted by coating HIV gp41 (100 μl of 10 μg/ml in 50 mM sodium carbonate pH 9.6 for 4 h at 4° C.) on a Nunc Maxisorp 96-well microtiter plate. After removing the coating solution, a blocking solution of 0.2% non-fat milk in PBS was applied. Caveolin-ΔTM, anti-His mouse monoclonal antibody (Sigma, H1029), and anti-mouse HRP-conjugated polyclonal antibody (1:2000, Sigma, A5906) were diluted in 100 μl PT buffer (1:1000, PBS, 0.05% Tween-20) and incubated for 1 h at 4° C. with four wash steps using PT buffer (200 μl). The ELISA was developed by the addition of 1% w/v o-phenylenediamine dihydrocholoride in citric acid buffer (0.02% w/v $H_2O_2$, 50 mM citric acid, 50 mM $Na_2HPO_4$, pH 5.0), and the absorbance of the solution was measured at 450 nm using a microtiter plate reader.

Shear Stress-Mediated Refolding of his-PKA Bound IMAC Resin and Activity Assays

The catalytic subunit of PKA was overexpressed in BL21 E. coli with an N-terminal $His_6$ tag by induction with IPTG (1 mM). This experiment applied the residual pellet from a 12 L culture, a waste product more typically discarded. After dissolution in lysis buffer, sonication was applied as described above. His-PKA was then denatured in 6 M guanidine-HCl, 20 mM sodium phosphate, 500 mM NaCl and incubated with $Ni^{2+}$-charged Profinity IMAC resin (Bio-Rad) for 2 h at room temperature (1 ml of a 1.72 mg/ml His-PKA to 50 μl or 250 μl bed volume IMAC). A control experiment used uncharged IMAC resin instead. The IMAC-His-PKA solution was then diluted to 1 M guanidine-HCl with binding buffer containing 1 mM imidazole, or with the elution buffer containing 500 mM imidazole as a control. This diluted solution was immediately treated in the VFD (1 ml, 5 krpm, 20 min). After transferring to a 1.5 ml Eppendorf tube, the resin was washed by aliquoting 1 ml wash buffer, inverting the tube three times, and centrifuging the tube at 2000×g for 2 min to separate the beads from the supernatant. This process was repeated two additional times before elution with elution buffer containing 500 mM imidazole. For protein quantification only, samples containing 500 mM imidazole were diluted 1:100 in wash buffer to prevent residual imidazole from interfering with the BCA assay. PKA activity was determined by monitoring substrate depletion in an NADH enzyme-linked assay at 340 nm (300 μl assay volume, 10 mM ATP, 0.5 mM NADH, 1 mM phosphoenolpyruvate, 0.0153 U/μl lactate dehydrogenase, 0.0269 U/μl pyruvate kinase, 0.67 mM kemptide, 100 mM MOPS, 9 mM MgCl2, pH 7.0). Kemptide was synthesized by solid-phase peptide synthesis. All other reagents were purchased from Sigma-Aldrich.

While embodiments of the present invention have been shown and described, various modifications may be made without departing from the scope of the present invention. The invention, therefore, should not be limited, except to the following claims, and their equivalents.

What is claimed is:

1. A method of protein refolding comprising:
   continuously loading a fluid containing a denatured protein into a vessel that is angled relative to horizontal, the vessel comprising an open end; and
   rotating the vessel along a longitudinal axis of the vessel at a rate within the range of about 3,000 RPM to about 9,000 RPM for a period of time to create a thin film of the fluid containing the denatured protein on an interior surface of the vessel and expose the denatured protein to shear force generated by rotation of the vessel so as to cause the denatured protein to refold; and
   continuously removing a portion of the fluid from the vessel during rotation of the vessel.

2. The method of claim 1, wherein the continuous loading of the fluid is delivered to the vessel via an inlet conduit terminating within the vessel.

3. The method of claim 2, wherein the portion of the fluid is continuously removed from the vessel via the open end of the vessel.

4. The method of claim 1, further comprising diluting the denatured protein in the fluid with a buffer solution prior to loading the vessel.

5. The method of claim 1, further comprising adjusting the temperature of the fluid contained within the vessel.

6. The method of claim 1, wherein the vessel is constantly rotated for between about 2.5 minutes to about 10 minutes.

7. The method of claim 1, wherein the vessel is angled within the range of about 20° to about 70°.

8. The method of claim 1, wherein the method is performed using a plurality of vessels.

9. The method of claim 1, further comprising controlling the temperature inside the vessel by heating and/or cooling through a jacket that at least partially surrounds the vessel.

10. The method of claim 1, wherein the vessel has an internal surface that is textured.

11. The method of claim 1, wherein the portion of the fluid that is continuously removed from the vessel is collected with a collector.

* * * * *